United States Patent [19]

Karp et al.

[11] Patent Number: 5,040,894

[45] Date of Patent: Aug. 20, 1991

[54] CUVETTE AND LINEAR DRIVE MECHANISM THEREFOR

[75] Inventors: Joseph G. Karp, Durham; Thomas B. Givens, Rougemont; John G. Link, Durham, all of N.C.

[73] Assignee: Akzo N.V., Arnhem, Netherlands

[21] Appl. No.: 443,956

[22] Filed: Dec. 1, 1989

[51] Int. Cl.⁵ ............................................. G01N 21/03
[52] U.S. Cl. ..................................... 356/246; 356/440
[58] Field of Search ...................... 356/246, 440, 435; 250/576

[56] References Cited

U.S. PATENT DOCUMENTS

| | | | |
|---|---|---|---|
| 4,067,653 | 1/1978 | Fletcher et al. | 356/433 |
| 4,305,723 | 12/1981 | Kolber et al. | 356/246 |
| 4,468,124 | 8/1984 | Berick | 356/435 |
| 4,665,553 | 5/1987 | Gershman et al. | 356/39 |

Primary Examiner—Richard A. Rosenberger
Attorney, Agent, or Firm—Spencer & Frank

[57] ABSTRACT

A cuvette for use in an optical instrument which includes a linear drive mechanism formed of a lead screw for positioning the cuvette along a linear path in the instrument. The cuvette has a body including at least one reaction well and an engaging feature for operatively engaging the threads of the lead screw so that the cuvette can be positioned along the linear path of the instrument. Preferably the reaction well of the cuvette has a trapezoid-shape cross section in a plane parallel to the optical path of the instrument in order to maximize the optical viewing area.

14 Claims, 2 Drawing Sheets

CUVETTE AND LINEAR DRIVE MECHANISM THEREFOR

BACKGROUND OF THE INVENTION

The present invention relates to a cuvette for use in an optical evaluation instrument and a device for positioning the cuvette along a linear path in the instrument.

Optical clinical laboratory instruments that evaluate a biochemical reaction taking place in a reaction well of a cuvette are known. In such an instrument, the cuvette is placed in an optical path of the instrument and a light beam, which passes through the cuvette, is received by light detectors. Evaluation of the output of the light detectors reflects changes in optical characteristics along the optical path caused by the biochemical reaction taking place in the reaction well of the cuvette. Such instruments are used to perform analysis relating to, for example, hemostasis, thrombosis, infectious diseases, and the like.

In one type of known optical instrument, a plurality of cuvettes are arranged in a one-piece circular tray and rotate around a fixed center position. This type of instrument is, at best, only semi-automatic. In another known optical instrument, a linear cuvette system makes it possible to have a walk-away automatic unit with an uninterrupted supply of cuvettes. Known, commercially available instruments using a linear cuvette system use a timing belt or steel belt for driving the cuvettes along a linear path. In these systems, teeth on the timing belt mate with corresponding teeth on the cuvettes and drag the cuvettes along the linear path. There are also systems that use combinations of rotary and linear cuvette drives. The timing belt, however, does not provide accurate positioning of the cuvette because there is a variation on the length of the belt that increases with the length of the belt (i.e., the longer the belt, the greater the tolerance). The placement of a cuvette relative to a fixed point on the path changes as the cuvette moves through the system in equal increments.

Optical evaluation systems are being developed which utilize small reaction volumes, on the order of 100 microliters, in the cuvette. In such systems, the positioning requirements for the cuvette are quite severe and are not satisfied by commercially available linear cuvette systems and the traditional timing belt drive mechanisms used therefor.

SUMMARY OF THE INVENTION

It is therefore an object of the invention to provide a cuvette and a linear drive mechanism therefor which will satisfy the positioning requirements of an optical evaluation instrument that is capable of working with small reaction volumes in the cuvette on the order of 100 microliters.

It is a further object of the invention to provide a cuvette for an optical evaluation instrument which can work with small reaction volumes and which provides the necessary optical characteristics and which maximizes the optical path cross-section of the light beam passing through the reaction volume in the cuvette in order to maximize the sensitivity of the instrument.

It is another object of the invention to provide a cuvette and drive mechanism therefor for use in an automated, high throughput optical evaluation system.

The above and other objects are accomplished according to the invention by the provision of a cuvette for use in an optical instrument that includes a linear drive mechanism formed of a lead screw for positioning the cuvette along the linear path in the instrument, wherein the body of the cuvette includes at least one reaction well and an engaging feature which engages the threads of the lead screw.

In a preferred embodiment of the invention, the reaction well of the cuvette has a trapezoid-shaped cross-section in a plane parallel to the optical path of the instrument.

Use of a lead screw, is known, for example, in the machine tool industry which uses lead screws to position equipment. The application of a lead screw for positioning a cuvette in an optical evaluation system is a simple, yet elegant and reliable solution for satisfying the higher accuracy requirements for cuvette positioning in instruments that employ micro-sampling. Additionally, the lead screw allows a greater variation in the loading position of the cuvette than does a timing belt because of the greater depth of tooth height relative to the timing belt. Further, shaping the reaction well of the cuvette to have a trapezoid, or wedge-shaped cross-section in a plane parallel to the optical path of the instrument maximizes the possible height of the microsample in the reaction well of the cuvette and maximizes the optical path cross-section of the microsample, thus maximizing the sensitivity of the instrument.

Additionally, the pitch of the lead screw can be selected so as to allow a desired relationship between the angular rotation of the screw and the linear travel of the cuvette.

Other advantageous features of the invention will become apparent from the detailed description below when considered in conjunction with the accompanying drawings and the appended claims.

DETAILED DESCRIPTION OF THE PREFERRED EMBODIMENTS

Figure 1:
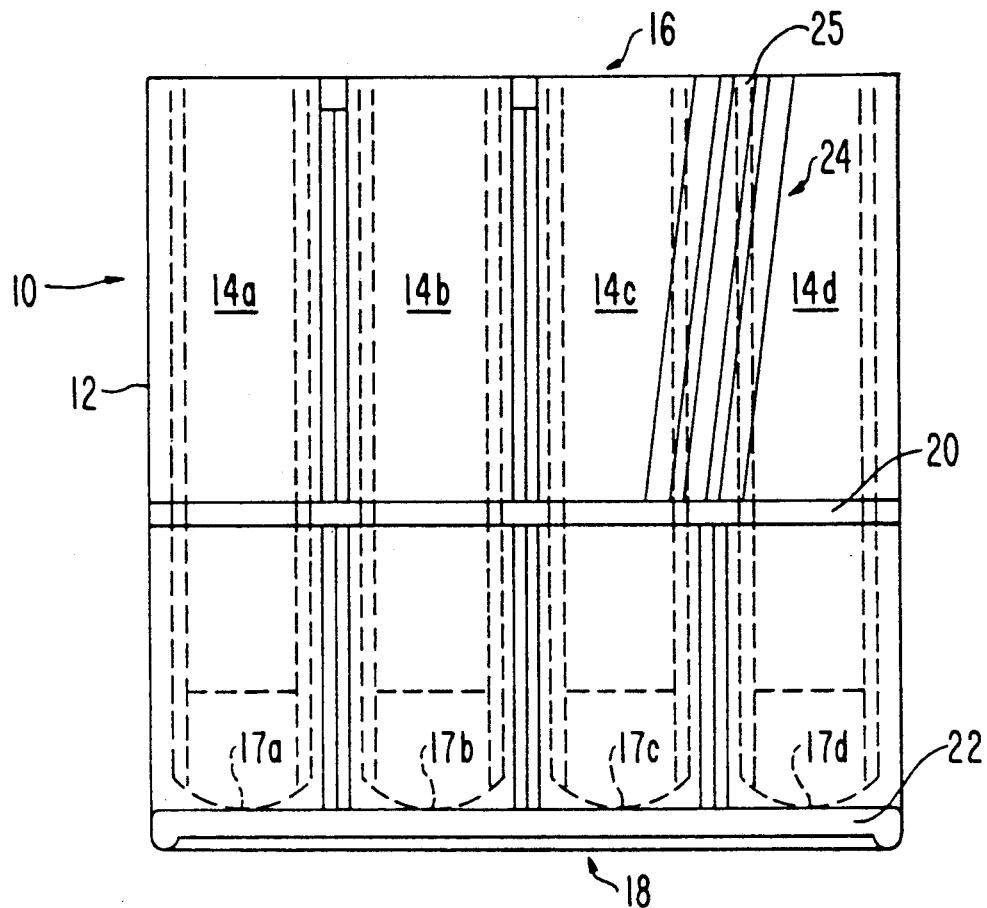
FIG. 1 is a front elevational view of a cuvette according to the invention.
Figure 2:
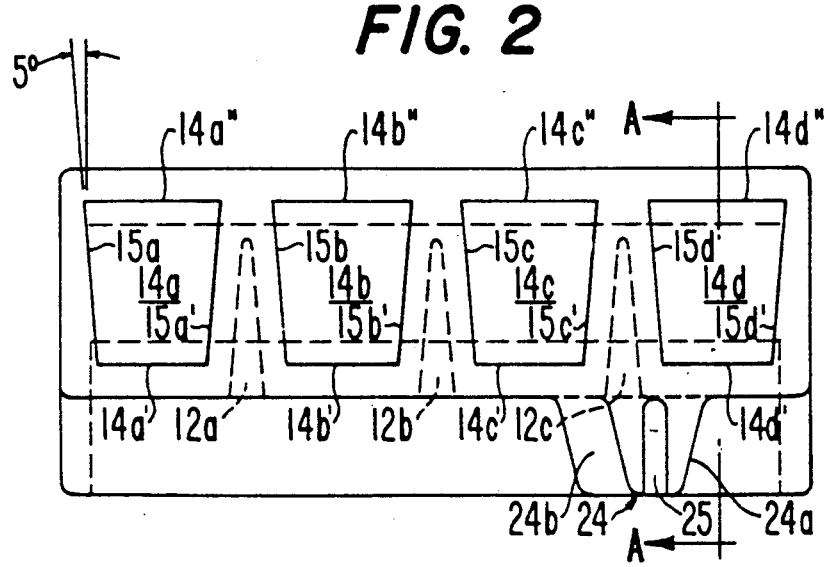
FIG. 2 is a top elevational view of FIG. 1.
Figure 3:
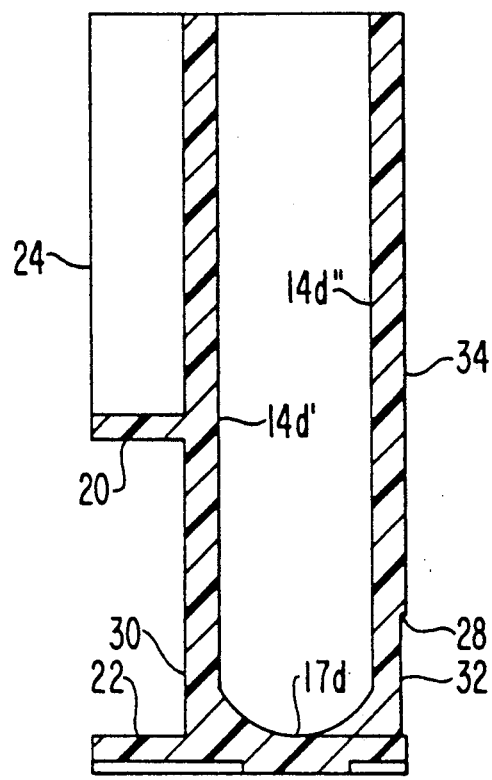
FIG. 3 is a cross-sectional view through line A—A of FIG. 2.

Referring to FIGS. 1 to 3, there is shown a cuvette 10 in accordance with the invention. Cuvette 10 comprises a unified cuvette body 12, containing four reaction wells, 14A, 14B, 14C and 14D. The reaction wells are open at the top end 16 of cuvette body 12 and are closed at the bottom end 18 of cuvette body 12. Reaction wells 14A to 14D each have a trapezoid-shaped cross-section in the horizontal plane, which is parallel to the optical path when the cuvette is positioned in an optical evaluation instrument for optical monitoring.

Reaction wells 14A to 14D, and viewed from the top in FIG. 2, have inner front walls 14A' to 14D', respectively, which are shorter than inner rear walls 14A" to 14 D", respectively. Reaction wells 14A to 14D each have non-parallel sidewalls 15A to 15D and 15A' to 15D', which form approximately a five degree angle with respect to a perpendicular line between front and rear parallel walls 14A', 14A"; 14B', 14B", etcetera.

The bottom of the reaction wells are formed by concave surfaces 17A to 17D, respectively. The concave bottom of the reaction well facilitates mixing of a reaction volume comprised of a sample volume and a diluent and/or a reagent.

The trapezoid-shaped cross-section of the reaction wells serves two purposes. First, because the cuvette of the invention is intended to be used with microvolumes on the order of 100 microliters, the trapezoidal shape of the reaction well maximizes the height of the reaction volume to insure a sufficient height for a light beam to pass through the reaction volume, below the mininicus of the reaction volume and above the concave bottom portion of the reaction well.

Second, the trapezoidal shape of the reaction well serves to maximize the optical path cross-section of the light beam passing through the reaction volume, which relates to the sensitivity of the optical monitoring instrument. That is, as cuvette 10 moves along a linear path by way of a drive mechanism to be described below, a light beam in the optical instrument will strike the cuvette at different angles other than perpendicular to inner front walls, 14A' to 14D', depending upon the location of cuvette 10, along the linear path which it traverses in the optical instrument.

Preferably, cuvette body 12 is provided with upper and lower flanges 20 and 22, respectively, which constitute guide surfaces for the cuvette in the instrument.

In accordance with the invention, cuvette body 12 is provided with a rib 24, which is at an angle with respect to the vertical in order to correspond to the pitch angle of the threads of a lead screw drive mechanism to be described in connection with FIGS. 4 and 5.

In the preferred embodiment, cuvette body 12 is made of a plastic, preferably acrylic, such as virgin Rohm and Haas VS 100 UVT, by injection molding techniques. In order to facilitate the injection molding process, it is desirable that the walls of cuvette body 10 are of substantially uniform thickness. Accordingly, cuvette body 10 is provided with recesses 12A, 12B and 12C between the reaction wells and with a recess 25 down the middle of rib 24.

In practice, a reaction volume in a reaction well of cuvette 10 will fill only the bottom portion of the reaction well to approximately the level of ledge 28, shown most clearly in FIG. 3. It is most important that the optical quality of cuvette 10 be greatest in the area below ledge 28, where the light beam will pass through the reaction volume. In particular, it is important that the outside front and rear surfaces 30 and 32, below ledge 20, be substantially parallel in order to minimize refraction, due to the cuvette, of the light beam passing through the reaction volume. In order to protect the optical quality of outer rear surface 32 during transport and handling, surface 32 is recessed slightly with respect to upper outer rear surface 34.

Figure 4:
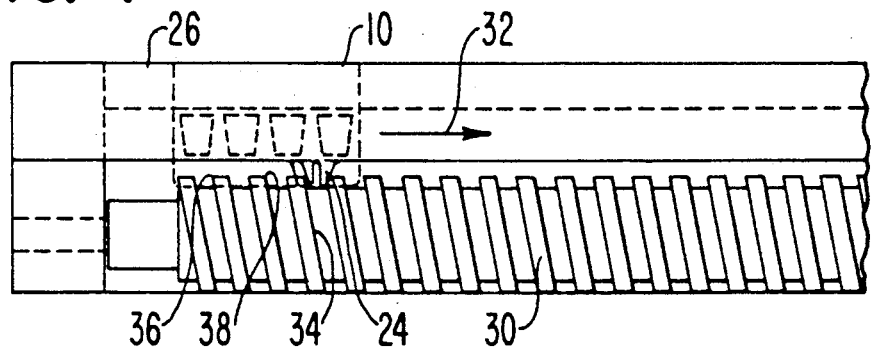
FIG. 4 is a top elevational view of a cuvette and lead screw drive mechanism according to the invention.
Figure 5:
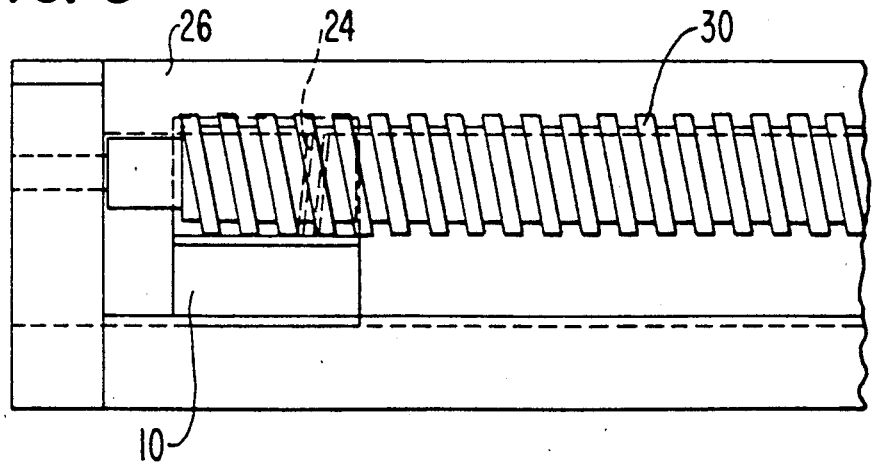
FIG. 5 is a front elevational view of FIG. 4.

Referring to FIGS. 4 and 5, there is shown a cuvette 10 of the type illustrated in FIGS. 1 to 3, in operative engagement with a lead screw 30, which, in accordance with the invention, is used to move cuvette 10 along a linear path in an optical evaluation instrument.

A linear track 26 holds cuvette 10 against lead screw 30 thereby limiting the motion of cuvette 10 to one axis. Rib 24 has a front surface 24A and a back surface 24B (see FIG. 2), which contact, respectively, oppositely facing surfaces or edges of the lead screw. Back surface 24B, of rib 24, provides movement in the direction of arrow 32 by virtue of its contact with driving edge 34 of the threads of lead screw 30, assuming appropriate rotation of lead screw 30.

On the other hand, front surface 24A of rib 24 limits backlash. Thus, as the screw rotates, cuvette 10 is driven linearly in track 26 as rib 24 of cuvette 10 moves through the continuous groove between the threads of the lead screw. Although a rib, which corresponds to an unrolled thread, is shown in FIGS. 4 and 5 for engaging the threads of lead screw 30, in practice two contact points or areas of different shapes which present corresponding front and back surfaces 24A and 24B, respectively, may be formed on cuvette 10 for contacting oppositely facing surfaces or edges of the threads on the lead screw. Thus, for example, two pyramid-shaped features may be formed on cuvette body 12, spaced apart in the direction of arrow 32, and positioned for contacting oppositely directed surfaces of the threads of lead screw 30. Furthermore, it is possible that such features be separated by one or more threads as long as they contact oppositely facing edges of the threads. For example, one feature could contact edge 36, and another feature could contact edge 38, as shown in FIG. 4.

Alternatively, and equally within the scope of the invention it is possible to have only one contact area for engaging the lead screw threads. Desirably, in this latter case, a biasing mechanism would additionally be employed to bias the cuvettes in a direction for avoiding backlash to assure precision in positioning the cuvettes.

Lead screw 30 is driven by a D.C. motor with an encoder (not shown), which may be programmed in accordance with the requirements of the optical instrument. The preferred embodiment uses a lead screw having a pitch equal to the required linear step distance traveled by the cuvette, i.e., that allows one revolution of the lead screw to equal the required travel of a cuvette reaction well from one optical station to the next. Such lead screws and D.C. motors with encoders are commercially available from a wide variety of sources and do not form, per se, part of the present invention. While the lead screw is commercially available per se, the pitch required may not be a standard, "off-the-shelf" item, depending on the width of a reaction well, thereby requiring a custom made lead screw.

Obviously, numerous and additional modifications and variations of the present invention are possible in light of the above teachings. It is therefore to be understood that within the scope of the appended claims, the invention may be practiced otherwise than a specifically claimed.

What is claimed is:

1. A cuvette for use in an optical instrument which includes a linear drive mechanism formed of a lead screw for positioning the cuvette along a linear path in the instrument, the lead screw having a thread presenting a driving flank, comprising:
   a cuvette body including at least one reaction well and engaging means, including a contact area formed on said body for contacting the driving flank of the thread of the lead screw, and for allowing the cuvette to be releasably engaged with the lead screw in a radial direction to the lead screw.

2. A cuvette as defined in claim 1, wherein the end of the lead screw has a trailing flank, said engaging means includes at least two contact areas formed on said body and being spaced from one another in the direction of the linear path for contacting the driving flank and the trailing flank, respectively, of the thread of the lead screw.

3. A cuvette as defined in claim 1, wherein said engaging means comprises at least one rib oriented at an angle corresponding to the pitch angle of the thread of the lead screw.

4. A cuvette as defined in claim 3, wherein said engaging means has only one said rib.

5. A cuvette as defined in claim 1 forming a combination with an optical instrument including a lead screw for operatively cooperating with said engaging means for positioning the cuvette along a linear path in said instrument.

6. A combination as defined in claim 5, wherein the thread of the lead screw has a trailing flank, and said engaging means includes at least two contact areas formed on said body and being spaced from one another in the direction of the linear path for contacting the driving flank and the trailing flank, respectively, of the thread of said lead screw.

7. A combination as defined in claim 5, wherein said engaging means comprises at least one rib oriented at an angle corresponding to the pitch angle of the thread of the lead screw.

8. A cuvette as defined in claim 1, wherein the optical instrument has an optical path and measures optical characteristics along the optical path in which the cuvette is disposed, and said at least one reaction well of the cuvette body has a trapezoid-shaped cross section in a plate parallel to the optical path of the instrument.

9. A cuvette as defined in claim 8, wherein said body has front and back outer surfaces with respect to the optical path of the instrument that ar substantially parallel to one another.

10. A cuvette as defined in claim 9, wherein said reaction well has front and back inner surfaces with respect to the optical path of the instrument, and said front inner surface has a width in a direction transverse to the optical path that is shorter than the corresponding width of said back inner surface.

11. A cuvette as defined in claim 8, wherein said at least one reaction well has a bottom which has a concave shape with respect to the interior of the reaction well.

12. A cuvette as defined in claim 8, wherein said body contains a plurality of linearly arranged, identically shaped, reactions wells.

13. A cuvette as defined in claim 1, wherein said engaging means comprises a sole projection formed on said body which presents said contact area.

14. A cuvette as defined in claim 1, wherein the cuvette body, when in an operative position in the optical instrument, has a vertical outer side wall parallel to the linear path of the instrument and said contact area is formed on said vertical outer side wall.

* * * * *